US012758754B2

(12) United States Patent
Traverso et al.

(10) Patent No.: US 12,758,754 B2
(45) Date of Patent: Oct. 13, 2026

(54) GRAVITY BASED DRUG DELIVERY DEVICE

(71) Applicant: Massachusetts Institute of Technology, Cambridge, MA (US)

(72) Inventors: Carlo Giovanni Traverso, Newton, MA (US); Niclas Roxhed, Bromma (SE); Siheng You, Somerville, MA (US); Graham Arrick, San Francisco, CA (US); Torben Sebastian Last, Sollentuna (SE)

(73) Assignee: Massachusetts Institute of Technology, Cambridge, MA (US)

( * ) Notice: Subject to any disclaimer, the term of this patent is extended or adjusted under 35 U.S.C. 154(b) by 740 days.

(21) Appl. No.: 18/031,269

(22) PCT Filed: Oct. 20, 2021

(86) PCT No.: PCT/US2021/055801
§ 371 (c)(1),
(2) Date: Apr. 11, 2023

(87) PCT Pub. No.: WO2022/087099
PCT Pub. Date: Apr. 28, 2022

(65) Prior Publication Data

US 2024/0017045 A1 Jan. 18, 2024

Related U.S. Application Data

(60) Provisional application No. 63/094,856, filed on Oct. 21, 2020.

(51) Int. Cl.
*A61M 31/00* (2006.01)
*A61M 5/172* (2006.01)
*A61M 39/22* (2006.01)

(52) U.S. Cl.
CPC .......... *A61M 31/002* (2013.01); *A61M 5/172* (2013.01); *A61M 39/22* (2013.01); *A61M 2205/33* (2013.01)

(58) Field of Classification Search
CPC .......... A61M 31/002; A61M 2210/106; A61M 2210/1064; A61M 2210/1053;
(Continued)

(56) References Cited

U.S. PATENT DOCUMENTS 8,759,284 B2 6/2014 Imran
2003/0073952 A1 4/2003 Flaherty et al.
(Continued)

FOREIGN PATENT DOCUMENTS

WO WO 2018/213576 11/2018
WO WO 2018/213579 11/2018
(Continued)

OTHER PUBLICATIONS

International Search Report and Written Opinion mailed Jan. 25, 2022, for Application No. PCT/US2021/055801.
(Continued)

*Primary Examiner* — Nilay J Shah
(74) *Attorney, Agent, or Firm* — Wolf, Greenfield & Sacks, P.C.

(57) ABSTRACT

A drug delivery device may be configured to delivery an active pharmaceutical ingredient (API) to a subject via the subject's oral-gastrointestinal (GI) tract. The drug delivery device may be configured to deliver a payload of an API while within the GI tract of the subject. The drug delivery device may include a reservoir, a potential energy source, a plurality of outlets, and a plurality of valves, wherein each outlet has a corresponding valve. The drug delivery device may further include a sensor configured to sense the direction of gravity, and the valves may be selectively opened
(Continued)

based on a sensed direction of gravity. Thus, the drug delivery device may dispense a dose of API within the GI tracts of the subject based at least in part on the sensed direction of gravity.

13 Claims, 5 Drawing Sheets

(58) Field of Classification Search
CPC .......... A61M 2210/1057; A61M 5/168; A61M 2205/33; A61M 5/172; A61M 2005/14204; A61B 2562/162; A61B 5/6861
See application file for complete search history.

(56) References Cited

U.S. PATENT DOCUMENTS

| | | | | |
|---|---|---|---|---|
| 2005/0182322 | A1 | 8/2005 | Grispo | |
| 2009/0082758 | A1 | 3/2009 | Gill et al. | |
| 2010/0042043 | A1* | 2/2010 | Krijnsen | A61M 5/1723 713/324 |
| 2011/0184235 | A1* | 7/2011 | Schostek | A61B 1/00158 600/109 |
| 2018/0070857 | A1* | 3/2018 | Jones | A61B 5/6861 |
| 2019/0282791 | A1* | 9/2019 | Jones | A61M 31/00 |

FOREIGN PATENT DOCUMENTS

| | | |
|---|---|---|
| WO | WO 2018/213582 | 11/2018 |
| WO | WO 2018/213593 | 11/2018 |
| WO | WO 2018/213600 | 11/2018 |

OTHER PUBLICATIONS

International Preliminary Report on Patentability mailed May 4, 2023, for Application No. PCT/US2021/055801.
Abramson et al., An ingestible self-orienting system for oral delivery of macromolecules. Science. Feb. 8, 2019;363(6427):611-615.
Debray et al., A low melting point alloy as a functional material for a one-shot micro-valve. J Micromech Microeng. Jun. 2007; 17: 1442.
Li et al., A Parylene MEMS Electrothermal Valve. J Microelectromech Syst. Dec. 2009; 18(6):1184-1197.

* cited by examiner

GRAVITY BASED DRUG DELIVERY DEVICE

CROSS-REFERENCE TO RELATED APPLICATIONS

This application is a national stage filing under 35 U.S.C. § 371 of International patent application serial number PCT/US2021/055801, filed Oct. 20, 2021, which claims the benefit of under 35 U.S.C. § 119(e) of U.S. provisional application Ser. No. 63/094,856, filed Oct. 21, 2020, the disclosure of each of which is incorporated herein by reference in its entirety.

FIELD

Disclosed embodiments relate to a drug delivery device to deliver, for example, an active pharmaceutical ingredient to a subject based at least partly on a direction of gravity.

BACKGROUND

Certain therapeutics are composed of large and complex molecules that denature readily when administered via the oral-gastrointestinal (GI) route. Accordingly, patients who need these therapeutics typically use more invasive forms of drug administration that are outside the GI route including, for example, subcutaneous injection.

BRIEF SUMMARY

In some embodiments, an article configured for administration to a subject includes a reservoir configured to contain an active pharmaceutical ingredient; a plurality of outlets; a plurality of valves, wherein each outlet of the plurality of outlets is in selective fluid communication with the reservoir through an associated valve of the plurality of valves; a sensor configured to sense a direction of gravity; and a processor configured to receive a signal from the sensor, wherein the processor is configured to operate one or more of the plurality of valves to dispense the active pharmaceutical ingredient through one or more of the plurality of outlets based at least in part on the sensed direction of gravity.

In some embodiments, a method of administering an active pharmaceutical ingredient to a subject includes sensing a direction of gravity; determining at least one outlet of a plurality of outlets that is oriented vertically downwards based on the sensed direction of gravity; opening at least one valve associated with the at least one outlet; and dispensing the active pharmaceutical ingredient through the at least one outlet.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
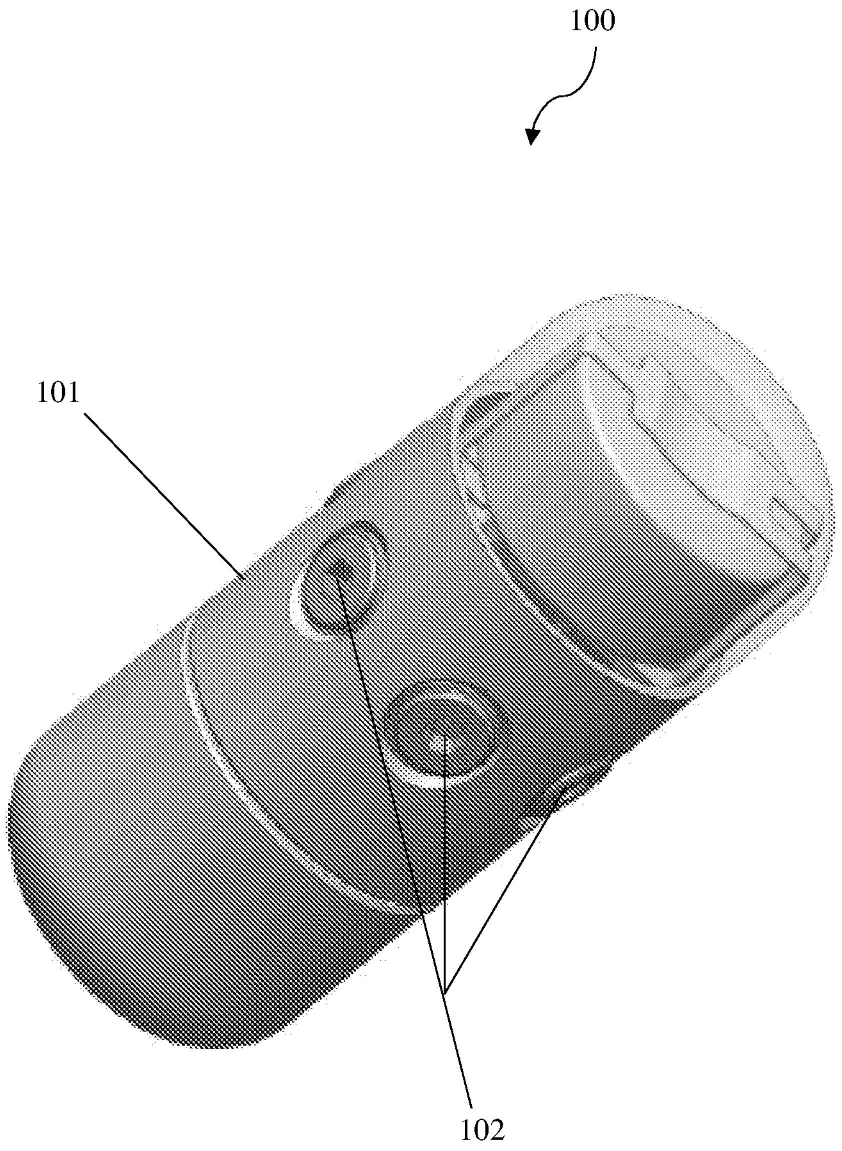
FIG. 1 is a perspective view of a drug delivery device according to one illustrative embodiment.

To treat a patient, a clinician may employ drugs consisting of large and complex molecules. Such molecules may denature readily when administered via the oral-gastrointestinal (GI) route, requiring a clinician to subject a patient to more invasive forms of drug administration, such as subcutaneous injection. The use of these more invasive forms of delivery sometimes lead to lapses in routine adherence and/or reduced quality of life for the patient. Moreover, in some instances, a clinician may wish to control how a drug is delivered within the GI tract. For example, a clinician may wish to have a drug delivered directly to the mucosal, submucosal, and/or other tissue within the GI tract of a subject, allowing the drug to quickly and precisely reach the blood stream of a patient.

In view of the above, the Inventors have recognized the advantages of a minimally invasive drug delivery device capable of delivering an active pharmaceutical ingredient (API) directly to the tissue of the GI tract. Particularly, in some instances, a clinician may employ an ingestible drug delivery device containing a one or more needle-free jet injectors configured to deliver a predetermined dosage of an API to the tissue of the GI tract to improve drug efficacy, while reducing patient discomfort. As used herein, the GI tract includes the esophagus, the stomach, the duodenum, the jejunum, the small intestine, and the large intestine.

To deliver an API directly to the tissue of the GI tract, the drug delivery device may include features that allow the drug delivery device to dispense the API in a desired direction. For example, in many instances, a drug delivery device may come into contact with the mucosa of the GI tract of a subject under the force of gravity. Accordingly, it may be preferable for the drug delivery device to deliver a jet of the API oriented in a direction that is approximately parallel with the direction of gravity. Due to the tissue of the GI tract being located beneath a drug delivery when it is at rest within the GI tract, when jetting an API in a direction that is approximately aligned with the direction of gravity, the drug delivery device may jet the API directly towards the mucosa, rather than into the intraluminal space within the GI tract away from the mucosa.

In some embodiments, a drug delivery device is configured to deliver an API to a subject in response to one or more predetermined conditions which may permit a device to actuate at a predetermined location within a subject. To administer the API, a patient may ingest the drug delivery device. As the drug delivery device reaches a predetermined point in the GI tract, the drug delivery device may actuate a potential energy source to deliver the API. The drug delivery device may also be capable of sensing the direction of gravity. When dispensing the API, the drug delivery device may deliver the API in the sensed direction of gravity. In some embodiments, the drug delivery device includes a plurality of outlets. The drug delivery device may be capable of selecting one of the plurality of outlets that is oriented at least partially in a vertically downwards direction relative to the sensed direction of gravity. The drug delivery device may then be capable of dispensing the API via the selected outlet. Thus, the drug delivery device may be capable of administering a jet of API directly into tissue of the GI tract underlying the device.

In some embodiments, a drug delivery device includes a reservoir, a plurality of outlets, a plurality of valves, a sensor, and a processor. The reservoir may be capable of holding a predetermined volume (i.e., dosage) of an API. The reservoir may be in selective fluid communication with the plurality of outlets via the plurality of valves. Each outlet of the plurality of outlets may be associated with a separate corresponding valve. Initially, the valves may be in a closed configuration such that the outlets are not in fluid communication with the reservoir. The valves may be capable of being selectively opened such that the reservoir is in fluid communication between with one or more desired outlets of the plurality of outlets to permit a flow of the API out of the one or more opened outlets. In addition to the above, the sensor may be capable of sensing a direction of gravity relative to the orientation of the drug delivery device. The sensor may output a signal to the processor corresponding to the sensed direction of gravity. The processor may then selectively operate one or more of the plurality of valves based at least partly on the signal from the sensor. For example, the processor may open one or more valves corresponding to one or more outlet that are oriented at least partially downwards relative to the sensed direction of gravity. This may then permit the API to flow out of the opened outlets in the form of one or more jets of API that are directed towards the underlying tissue of the GI tract.

As described above, the processor may select an outlet from a plurality of outlets of the drug delivery device for dispensing a dose of an API based on a sensed direction of gravity. In some embodiments, the outlets may be distributed around an exterior of the device to permit jets to be emitted in any number of different directions. For example, the plurality of outlets may be disposed on a perimeter of the drug delivery device in a generally circular arrangement. Depending on the application, the drug delivery device may also include a sufficient number of outlets such that an angular spacing between the outlets around a perimeter of a device may be less than or equal to 90 degrees, 45 degrees, 30 degrees, and/or any other appropriate spacing. Accordingly, when a device is at rest on a surface, at least one outlet of the plurality of outlets may be oriented in a direction that is aligned within 45 degrees, 22.5 degrees, 15 degrees, and/or any other appropriate direction relative to the sensed direction of gravity. In such an embodiment, a processor may compare the angle between a direction of orientation of each outlet and the sensed direction of gravity. The processor may then dispense the API through the outlet, or outlets, having the lowest angular difference relative to the sensed direction of gravity. For example, if there are two outlets that are approximately equally spaced from the direction of gravity, the processor may operate either one, or both, of the outlets simultaneously, which may improve the reliability of the drug delivery device. Of course, the arrangement of outlets need not be circular and the outlets do not necessarily need to be spaced equally around a perimeter of a device as other outlet arrangements and any appropriate number of outlets are contemplated (e.g., rectangular, triangular, square, or other suitable arrangement).

It should be understood that any appropriate sensor capable of monitoring a direction of gravity may be used with the currently disclosed drug delivery devices. For example, appropriate sensors may include, but are not limited to, a gravitometer, one or more accelerometers, a three-axis accelerometer, an inertial monitoring unit (IMU), and/or any other sensor capable of sensing a local direction of gravity.

Depending on the specific type of valve used in a drug delivery device, a processor may selectively operate the one or more valves of a device in any suitable manner. For example, in some embodiments, the valves are electrically actuated. Accordingly, the processor may provide a current to the electrically actuated valve to selectively open and close the valve. In some embodiments, each valve of the drug delivery device may include a corresponding rupturable membrane. For example, a given rupturable membrane may be a heat rupturable membrane associated with a heater. To open such a valve, the processor may operate the heater to heat the heat rupturable membrane, thus rupturing the membrane and opening the associated outlet. In some embodiments, the rupturable membrane is configured to be electrolytically degradable. To open such a valve, the processor may provide a current and/or voltage potential between an electrolytically dissolvable portion of the valve and an associated electrode to open the valve. Of course, it should be understood that any valve capable of being opened by an associated processor, including mechanically actuated valves, may also be used as the disclosure is not limited to any particular valve construction.

Depending on the embodiment, a processor may also be configured to actuate a potential energy source of a drug delivery device. For example, in some embodiments, the processor may provide an electrical current to the potential energy source to activate it, when appropriate. Of course, the processor need not actuate the potential energy source as the potential energy source may be activated separately from the processor by a separate trigger and/or the potential energy source may be pre-energized such that the reservoir is already pressurized prior to opening of the one or more valves of a device (e.g. a preloaded spring, compressed gas, or other construction). For example, the potential energy source may be actuated by a mechanical process, a chemical process, or other suitable process. Alternatively, a separate trigger, including any of those described herein, may be used for actuating the potential energy source as the disclosure is not limited to how a potential energy source applies a driving force to expel an API from a reservoir of a drug delivery device. Additionally, in such embodiments, triggering of the potential energy source may occur either prior to, at the same time, or after actuation of a trigger to open one or more valves of the drug delivery device.

In addition to the above, the Inventors have recognized the advantages of an ingestible drug delivery device having a trigger mechanism for releasing the API at a predetermined location within the GI tract. According to exemplary embodiments described herein, a jet may be triggered by one or more predetermined conditions associated with a desired location within the GI tract of a subject. In some embodiments, the predetermined condition includes one or more of a predetermined time after ingestion of the drug delivery device, a predetermined location in the GI tract, physical contact with the GI tract, physical manipulation in the GI tract (e.g., compression via peristalsis), one or more characteristics of the GI tract (e.g., pH, pressure, acidity, temperature, etc.), or combinations thereof. Upon actuation, the operating parameters of the jet may be appropriately selected such that the jet is emitted from the drug delivery device with sufficient velocity such that the jet penetrates a tissue of the gastrointestinal tract of the subject adjacent to the drug delivery device.

Embodiments disclosed herein relate to an ingestible delivery device equipped with one or more jet injectors for delivery of an API. Such an article has numerous benefits. First, an ingestible drug delivery device may not include sharp points. Second, the jet injectors of such a drug delivery device do not require the numerous moving parts associated with actuating and/or retracting a needle, thereby reducing system complexity and cost relative to needle-based systems. The use of jet deployed APIs may also result in significant increases in the bioavailability of the API on par with subcutaneous injections as compared to other ingested API's provided with common chemical permeation enhancers (approximately 2% bioavailability). Further, such needle-free drug delivery systems may result in less pain and/or trauma for the subject at the site of injection relative to needle-based delivery, as well as enhanced pharmacokinetics (PK).

In some embodiments, the drug delivery device includes a potential energy source for pushing (i.e., dispensing) the API from the reservoir through the outlet. According to exemplary embodiments described herein, a drug delivery device includes a potential energy source which is used to store energy in the drug delivery device that is used to generate a jet of the API when the drug delivery device is actuated. In some embodiments, the potential energy source may be a compressed gas. The compressed gas may be directly stored in the drug delivery device, or the compressed gas may be generated via a chemical reaction or phase change. For example, in some embodiments dry ice may be stored in a chamber of the drug delivery device so that compressed gas is generated as the dry ice sublimates. Alternatively, a compressed gas may be provided to a desired chamber prior to sealing a drug delivery device. In some embodiments, the potential energy source may be a spring (e.g., a compressed compression spring). In some embodiments, the potential energy source may be a reaction chamber. For example, the reaction chamber may allow an acid and base to be combined to generate gas, leading the leading to the expulsion of API the drug delivery device is actuated. Alternatively, in another embodiment, a trigger may detonate an explosive material located within a chamber to generate pressurized gas for expelling the API from the drug delivery device. Of course, any suitable reaction or other potential energy source may be employed to pressurize and drive an API in a jet when a drug delivery device is actuated, as the present disclosure is not so limited.

According to exemplary embodiments described herein, a drug delivery device includes a potential energy source configured to pressurize an API so that the API may be released in a jet into a GI tract mucosal lining. The pressure applied to the reservoir may affect jetting power and/or a jet velocity of an API jet emitted by the drug delivery device. In some embodiments, the potential energy source may apply a pressure to an API reservoir less than or equal to 1000 bar, 800 bar, 600 bar, 500 bar, 250 bar, 100 bar, 60 bar, 40 bar, 10 bar, 1 bar, and/or any other appropriate pressure. Correspondingly, the potential energy source may apply a pressure to an API reservoir greater than or equal to 0.1 bar, 1 bar, 10 bar, 40 bar, 60 bar, 100 bar, 250 bar, 500 bar, 600 bar, 800 bar, and/or any other appropriate pressure. Combinations of the above-noted ranged are contemplated, including, but not limited to, pressures between 0.1 bar and 1000 bar, between 0.1 bar and 800 bar, between 0.1 bar and 600 bar, between 0.1 bar and 500 bar, between 0.1 bar and 250 bar, between 0.1 bar and 100 bar, between 0.1 bar and 60 bar, between 0.1 bar and 40 bar, between 0.1 bar and 10 bar, between 0.1 bar and 1 bar, between 1 bar and 1000 bar, between 1 bar and 800 bar, between 1 bar and 600 bar, between 1 bar and 500 bar, between 1 bar and 250 bar, between 1 bar and 100 bar, between 1 bar and 60 bar, between 1 bar and 40 bar, between 1 bar and 10 bar, between 10 bar and 1000 bar, between 10 bar and 800 bar, between 10 bar and 600 bar, between 10 bar and 500 bar, between 10 bar and 250 bar, between 10 bar and 100 bar, between 10 bar and 60 bar, between 10 bar and 40 bar, between 10 bar and 800 bar, between 10 bar and 600 bar, between 10 bar and 500 bar, between 10 bar and 250 bar, between 10 bar and 100 bar, between 10 bar and 60 bar, between 10 bar and 40 bar, between 40 bar and 800 bar, between 40 bar and 600 bar, between 40 bar and 500 bar, between 40 bar and 250 bar, between 40 bar and 100 bar, between 40 bar and 60 bar, between 60 bar and 800 bar, between 60 bar and 600 bar, between 60 bar and 500 bar, between 60 bar and 250 bar, between 60 bar and 100 bar, between 100 bar and 800 bar, between 100 bar and 600 bar, between 100 bar and 500 bar, between 100 bar and 250 bar, between 250 bar and 800 bar, between 250 bar and 600 bar, between 250 bar and 500 bar, between 500 bar and 800 bar, between 500 bar and 600 bar, or between 600 bar and 800 bar. Of course, any suitable pressure may be applied to an API reservoir, as the present disclosure is not so limited.

To achieve the exemplary jetting powers described herein, a jet generated by a drug delivery device of exemplary embodiments described herein may have a corresponding velocity. Accordingly, in some embodiments, a drug delivery device may be configured to generate a jet having a velocity less than or equal to 250 m/s, 200 m/s, 150 m/s, 100 m/s, 75 m/s, 50 m/s, and/or another appropriate velocity. Correspondingly, a drug delivery device may be configured to generate a jet having a velocity greater than or equal to 20 m/s, 30 m/s, 50 m/s, 100 m/s, 150 m/s, 200 m/s, and/or another appropriate velocity. Combinations of the above-noted ranges are contemplated, including, but not limited to, jet velocities between 20 m/s and 250 m/s, between 20 m/s and 200 m/s, between 20 m/s and 100 m/s, between 20 m/s and 150 m/s, between 20 m/s and 100 m/s, between 20 m/s and 75 m/s, between 20 m/s and 50 m/s, between 50 m/s and 250 m/s, between 50 m/s and 200 m/s, between 50 m/s and 100 m/s, between 50 m/s and 150 m/s, between 50 m/s and 100 m/s, between 50 m/s and 75 m/s, between 75 m/s and 250 m/s, between 75 m/s and 200 m/s, between 75 m/s and 100 m/s, between 75 m/s and 150 m/s, between 75 m/s and 100 m/s, between 100 m/s and 250 m/s, between 100 m/s and 200 m/s, between 100 m/s and 150 m/s, between 150 m/s and 250 m/s, between 150 m/s and 200 m/s, or between 200 m/s and 250 m/s. Of course, any jet velocity suitable to deliver an API to a GI mucosal lining, or other structure associated with the GI tract of a subject, may be employed, as the present disclosure is not so limited.

In some embodiments, a maximum transverse dimension of an outlet and/or jet (e.g. a diameter) may be less than or equal to 350 μm, 300 μm, 250 μm, 200 μm, 150 μm, 100 μm, 75 μm, 50 μm, 25 μm, 10 μm, and/or any other appropriate dimension. Correspondingly, an outlet and/or jet maximum transverse dimension may be greater than or equal to 5 μm, 10 μm, 25 μm, 50 μm, 75 μm, 100 μm, 150 μm, 200 μm, 250 μm, 300 μm, and/or any other appropriate dimension. Combinations of the above-noted ranges are contemplated, including, but not limited to, maximum transverse dimensions of a jet and/or outlet between 5 μm and 350 μm, between 10 μm and 350 μm, between 25 μm and 350 μm, between 50 μm and 350 μm, between 75 μm and 350 μm, between 100 μm and 350 μm, between 150 μm and 350 μm, between 200 μm and 350 μm, between 250 μm and 350 μm, between 300 μm and 350 μm, between 5 μm and 300 μm, between 10 μm and 300 μm, between 25 μm and 300 μm, between 50 μm and 300 μm, between 75 μm and 300 μm, between 100 μm and 300 μm, between 150 μm and 300 μm, between 200 μm and 300 μm, between 250 μm and 300 μm, between 5 μm and 250 μm, between 10 μm and 250 μm, between 25 μm and 250 μm, between 50 μm and 250 μm, between 75 μm and 250 μm, between 100 μm and 250 μm, between 150 μm and 250 μm, between 200 μm and 250 μm, between 5 μm and 200 μm, between 10 μm and 200 μm, between 25 μm and 200 μm, between 50 μm and 200 μm, between 75 μm and 200 μm, between 100 μm and 200 μm, between 150 μm and 200 μm, between 5 μm and 150 μm, between 10 μm and 150 μm, between 25 μm and 150 μm, between 50 μm and 150 μm, between 75 μm and 150 μm, between 100 μm and 150 μm, between 5 μm and 100 μm, between 10 μm and 100 μm, between 25 μm and 100 μm, between 50 μm and 100 μm, between 75 μm and 100 μm, between 5 μm and 75 μm, between 10 μm and 75 μm, between 25 μm and 75 μm, between 50 μm and 75 μm, between 5 μm and 50 μm, between 10 μm and 50 μm, between 25 μm and 50 μm, between 5 μm and 25 μm, between 10 μm and 25 μm, or between 5 μm and 10 μm. Of course, any jet diameter suitable for delivery of an API to a GI mucosal lining may be employed, as the present disclosure is not so limited.

A drug delivery device of exemplary embodiments described herein may be configured to deliver a predetermined dose of an API to a subject. According to exemplary embodiments described herein, a drug delivery device may include an API reservoir volume less than or equal to 500 μL, 300 μL, 200 μL, 150 μL, 100 μL, 75 μL, 50 μL, 25 μL, 10 μL, and/or any other appropriate volume. Correspondingly, a drug delivery device may contain an API reservoir volume greater than or equal to 1 μL, 5 μL, 10 μL, 25 μL, 50 μL, 75 μL, 100 μL, 200 μL, 300 μL, and/or any other appropriate volume. Combinations of the above-noted volumes are contemplated, including, but not limited to, reservoir volumes between 1 μL and 500 μL, between 1 μL and 300 μL, between 1 μL and 200 μL, between 1 μL and 150 μL, between 1 μL and 100 μL, between 1 μL and 75 μL, between 1 μL and 50 μL, between 1 μL and 25 μL, between 1 μL and 10 μL, between 10 μL and 500 μL, between 10 μL and 300 μL, between 10 μL and 200 μL, between 10 μL and 150 μL, between 10 μL and 100 μL, between 10 μL and 75 μL, 10 μL and 50 μL, between 10 μL and 25 μL, between 25 μL and 500 μL, between 25 μL and 300 μL, between 25 μL and 200 μL, between 25 μL and 150 μL, between 25 μL and 100 μL, between 25 μL and 75 μL, between 25 μL and 50 μL, between 50 μL and 500 μL, between 50 μL and 300 μL, between 50 μL and 200 μL, between 50 μL and 150 μL, between 50 μL and 100 μL, between 50 μL and 75 μL, between 75 μL and 500 μL, between 75 μL and 300 μL, between 75 μL and 200 μL, between 75 μL and 150 μL, between 75 μL and 100 μL, between 100 μL and 500 μL, between 100 μL and 300 μL, between 100 μL and 200 μL, between 100 μL and 150 μL, between 150 μL and 500 μL, between 150 μL and 300 μL, between 150 μL and 200 μL, between 200 μL and 500 μL, between 200 μL and 300 μL, or between 300 μL and 500 μL. Of course, any suitable reservoir volume may be employed in a drug delivery device, as the present disclosure is not so limited.

In some embodiments, a drug delivery device is sized and shaped to be ingested by a subject. Accordingly, the drug delivery device may be appropriately small so that the drug delivery device may be easily swallowed and subsequently pass through the GI tract, including the esophagus and pyloric opening within the stomach. In some embodiments, a drug delivery device may include an overall length, such as a maximum dimension along a longitudinal axis of the device, that is less than or equal to 40 mm, 30 mm, 20 mm, 10 mm, 5 mm, and/or another appropriate length. Correspondingly, a drug delivery device may have an overall length greater than or equal to 3 mm, 5 mm, 10 mm, 20 mm, 25 mm, and/or another appropriate length. Combinations of the above-noted ranges are contemplated, including, but not limited to, overall lengths between 5 mm and 30 mm, between 10 mm and 30 mm, between 20 mm and 30 mm, between 25 mm and 30 mm, between 5 mm and 25 mm, between 10 mm and 25 mm, between 20 mm and 25 mm, between 5 mm and 20 mm, between 10 mm. In some embodiments, a drug delivery device may have a maximum external transverse dimension, such as a diameter or other dimension that may be perpendicular to the longitudinal axis, that is less than or equal to 11 mm, 10 mm, 7 mm, 5 mm, and/or another appropriate dimension. Correspondingly, a drug delivery device may have a maximum external transverse dimension greater than or equal to 3 mm, 5 mm, 7 mm, 9 mm, and/or another appropriate dimension. Combinations of the above-noted ranges are contemplated, including, but not limited to, maximum external transverse dimensions between 3 mm and 11 mm, between 3 mm and 10 mm, between 3 mm and 7 mm, between 3 mm and 5 mm, between 5 mm and 11 mm. In some embodiments, a drug delivery device may have an overall volume less than or equal to 3500 $mm^3$, 3000 $mm^3$, 2500 $mm^3$, 2000 $mm^3$, 1500 $mm^3$, 1000 $mm^3$, 750 $mm^3$, 500 $mm^3$, 250 $mm^3$, 100 $mm^3$, and/or any other appropriate volume. Corresponding, a drug delivery device may have an overall volume greater than or equal to 50 $mm^3$, 100 $mm^3$, 250 $mm^3$, 500 $mm^3$, 750 $mm^3$, 1000 $mm^3$, 1500 $mm^3$, 2000 $mm^3$, 2500 $mm^3$, and/or any other appropriate volume. Combinations of the above-noted ranged are contemplated, including, but not limited to, volumes between 1000 $mm^3$ and 3000 $mm^3$, 1500 $mm^3$ and 3000 $mm^3$, 50 $mm^3$ and 500 $mm^3$, 50 $mm^3$ and 100 $mm^3$, as well as 2000 $mm^3$ and 3000 $mm^3$. Of course, any suitable overall length, maximum external transverse dimension, and volume for an ingestible delivery device may be employed, as the present disclosure is not so limited.

According to exemplary embodiments described herein, a trigger of a drug delivery device may be configured to actuate the drug delivery device in the GI tract of a subject under a predetermined condition. In some embodiments, the predetermined condition includes one or more of a predetermined time after ingestion of the drug delivery device, a predetermined location in the GI tract, physical contact with the GI tract, physical manipulation in the GI tract (e.g., compression via peristalsis), one or more characteristics of the GI tract (e.g., pH, pressure, temperature, etc.), or combinations thereof. In some embodiments, the trigger may be a passive component configured to interact with the environment of the GI tract to actuate the drug delivery device. For example, in some embodiments the trigger may be a sugar plug, or other dissolvable material, configured to dissolve in the GI tract. The dissolvable plug may have a certain thickness and/or shape that at least partly determines the speed at which the sugar plug dissolves and ultimately actuates the drug delivery device. In some embodiments, the trigger has an oval shape, an egg shape, a spherical shape, an elliptical shape, a cylindrical shape, a conical shape, or a spherocylindrical shape. In another embodiment, the trigger may be at least partially formed by an enteric coating. For example, in some embodiments, a trigger may include both a sugar plug and an enteric coating, as the present disclosure is not so limited. Other appropriate materials for a dissolvable trigger may include, but are not limited to, sugar alcohols, such as disaccharides (e.g. Isomalt), water soluble polymers, such as Poly-vinyl alcohol, enteric coatings, time-dependent coatings, enteric and time-dependent coatings, temperature-dependent coatings, light-dependent coatings, and/or any other appropriate material capable of being dissolved within the GI tract of a subject. In some embodiments, a trigger may include a triggerable membrane including EDTA, glutathione, or another suitable chemical. In some embodiments, a sugar alcohol trigger may be employed in combination with an enteric coating configured to protect the sugar alcohol trigger until the drug delivery device is received in the GI tract of a subject. In some embodiments, the trigger may include a pH responsive coating to assist with delaying triggering until after ingestion. In some embodiments, the trigger may be a sensor that detects one or more characteristics of the GI tract. For example, a sensor detecting contact with a GI mucosal lining may be used to actuate the device. Other types of triggers may include an electrical timer, a light sensor, an enzymatic sensor, a conductivity sensor, a pH sensor, a pressure sensor, a temperature sensor, and/or any other appropriate sensor or construction capable of providing a signal to a processor or closing an electrical circuit associated with a processor or other portion of the device when that the device is exposed to one or more predetermined conditions corresponding to a desired target location within the GI tract or other anatomical structure of a subject. Accordingly, it should be understood that the triggers disclosed herein are not limited to any specific type or construction of trigger.

Depending on the application, the trigger may be constructed to actuate on any suitable timescale (e.g., a predetermined time after ingestion of the drug delivery device). In some instances, the timescale may vary depending on a target anatomical structure of the drug delivery device. For example, to actuate the drug delivery device within the esophagus of a subject, the trigger may actuate between 30 and 60 seconds inclusive after the subject ingests the drug delivery device. To actuate the drug delivery device within the stomach of a subject, the trigger may actuate between 5 and 9 minutes inclusive after the subject ingests the drug delivery device. To actuate the drug delivery device within the small intestine of a subject, the trigger may actuate between 1 and 4 hours inclusive after the subject ingests the drug delivery device. To actuate the drug delivery device within the colon of a subject, the trigger may actuate between 6 and 14 hours inclusive after the subject ingests the drug delivery device. Other timescales for actuating the drug delivery device are also contemplated, as the disclosure is not so limited.

According to exemplary embodiments described herein, the drug delivery device is administered to a subject orally. In other embodiments, the drug delivery device may be administered, rectally, vaginally, or nasally as the present disclosure is not so limited. Additionally, in some cases a drug delivery device according to exemplary embodiments described herein may be implanted into an organ of a subject. For example, a drug delivery device may be implanted into the arm, brain, peritoneum, etc. of the subject.

As used herein, the term “active pharmaceutical ingredient” (also referred to as a “drug” or “therapeutic agent”) refers to an agent that is administered to a subject to treat a disease, disorder, or other clinically recognized condition, or for prophylactic purposes, and has a clinically significant effect on the body of the subject to treat, prevent, and/or diagnose the disease, disorder, or condition. The active pharmaceutical ingredient may be delivered to a subject in a quantity greater than a trace amount to affect a therapeutic response in the subject. In some embodiments, active pharmaceutical ingredients (APIs) can include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and biopharmaceuticals. Certain such APIs may include molecules such as proteins, peptides, hormones, nucleic acids, gene constructs, etc., for use in therapeutic, diagnostic, and/or enhancement areas. In certain embodiments, the API is a small molecule and/or a large molecule. Further, while according to exemplary embodiments described herein a drug delivery device may generate an incompressible jet of a liquid API, in other embodiments a jet of an API generated by a drug delivery device may be formed of gases, viscous fluids, aerosolized powders, and/or other appropriate type of API, as the present disclosure is not so limited. Accordingly, it should be understood that the API’s described herein are not limited to any particular type of API.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 shows a perspective view of one embodiment of a drug delivery device 100. Drug delivery device 100 may include a plurality of outlets 102. In some embodiments, the plurality of outlets 102 are disposed around a perimeter of a portion of the exterior housing 101 of the device that is configured to contact underlying tissue of the gastrointestinal tract the device is disposed against after ingestion. It should be understood that while a particular arrangement of outlets 102 with a particular nozzle shape have been illustrated in the figure, any appropriate number of outlets with any appropriate nozzle geometry may be used as the disclosure is not limited in this fashion.

Figure 2A:
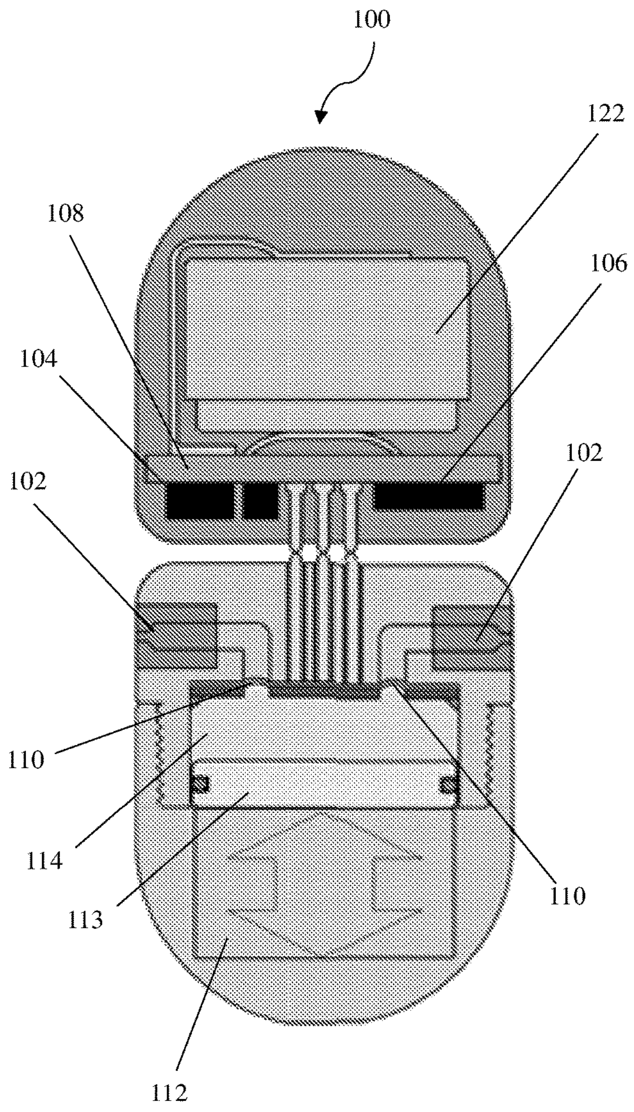
FIG. 2A is a cross sectional view of a drug delivery device according to one illustrative embodiment.

FIG. 2A shows a cross sectional view of a drug delivery device 100. The drug delivery device 100 may include a potential energy source 112, a reservoir 114, a plurality of valves 110, a printed circuit board 108, a sensor 104 configured to sense a direction of gravity, a processor 106, and a power source 122. The reservoir 114 may be configured to hold a predetermined dose of an API. Additionally, the processor is connected with the sensor such that a signal associated with the sensed direction of gravity may be output by the sensor to the processor. Based on the sensed direction of gravity, and other predetermined conditions elaborated on below, the processor may operate the device to deliver an API to a subject as elaborated on below.

In some embodiments, a piston 113 may be slidably disposed within an interior volume of the housing of the device such that the piston is disposed between the potential energy source and the reservoir. The reservoir 114 holds the dose of the API until the potential energy source 112 displaces the piston into the reservoir, or otherwise applies a force to eject the API from the reservoir 114 through one or more of the outlets 102 in selective fluid communication with the reservoir through the associated valves. In some instances, it may be desirable to isolate the API within the reservoir from an exterior environment surrounding the device. In such an embodiment, the reservoir 114 may include a metallic or otherwise non-fluid permeable barrier or lining (not illustrated). The barrier or lining may be hermetically sealed by a metallic binding process, such as hot welding, mechanical compression, cold bonding, soldering, electrochemical bonding or other suitable bonding method.

In some embodiments, the drug delivery device 100 may include a printed circuit board (PCB) 108 to facilitate electronic communication between the electrical components of the drug delivery device 100. For example, as shown in FIG. 2A, PCB 108 may be electronically connected to the sensor 104 and the processor 106. Thus, the sensor 104 may connected with the processor 106 through the PCB. The power source 122 may also be connected to the PCB 108. Thus, the processor 106 may be able to selectively operate various components of the device using power provided by the power source 122. Of course, the power source 122, the sensor 104 and the processor 106 need not be disposed on the PCB 108, as these components may be operatively connecting in any suitable manner.

As noted above, a drug delivery device 100 may include a plurality of valves 110 that are configured to selectively permit or prevent fluid communication between a reservoir 114 and one or more associated outlets 102 of the device. Specifically, the plurality of valves 110 may be in an initially closed state to prevent the flow of an API through the outlets prior to one or more of the valves being opened. In the open state, the reservoir is in fluid communication with the outlet associated with the one or more open valves, and the API contained in the reservoir 114 may flow through the drug delivery device 100 via the one or more open outlets 102. In some instances, each valve of the plurality of valves 110 may be located along a flow path fluidly connected to either an individual outlet or a plurality of outlets 102. Thus, the drug delivery device 100 may control which outlet, or outlets, of the plurality of outlets 102 dispense API from the reservoir 114.

Figure 2B:
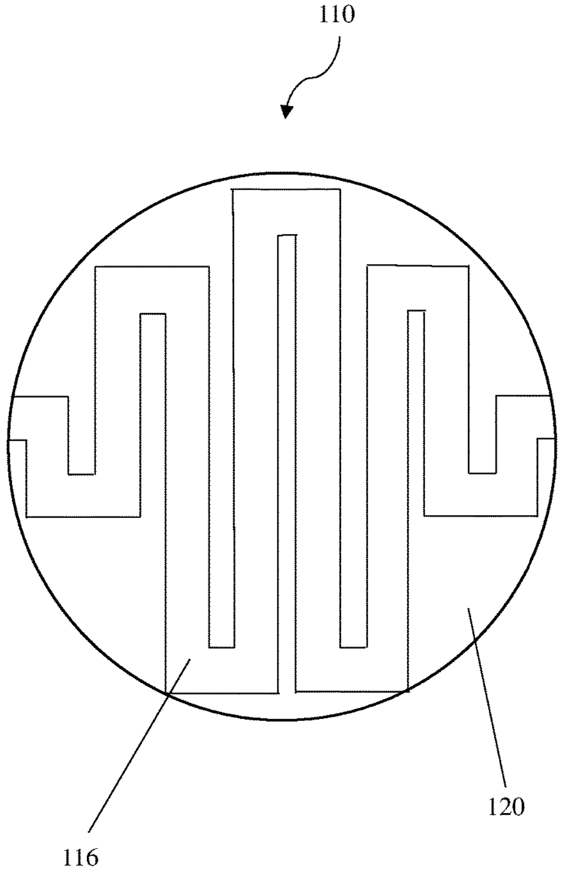
FIG. 2B is a cross sectional view of a valve of a drug delivery device according to one illustrative embodiment.

One example of a valve that may be used with a drug delivery device is shown in FIG. 2B. In the depicted embodiment, each valve 110 includes a rupturable membrane 120 and a heater 116 that is electrically connected to a power source, such as a battery. Depending on the embodiment, the heater may correspond to a conductive material embedded in, or deposited on, the membrane where a current that passes through the conductive path formed by the conductive material may resistively heat the membrane. The material may be deposited in a pattern, such as the serpentine pattern shown in the figures, to apply heat from the heater to an increased area of the membrane. To operate the valve, a current may be passed through the conductive material of the heater to heat the rupturable membrane to a desired temperature to soften the membrane. As the membrane is heated to the desired opening temperature, pressure applied to the membrane by the pressurized API may rupture the softened membrane while leaving the other unheated membranes intact. Alternatively, and without wishing to be bound by theory, rupturable membrane 120 may rupture when the heater 116 thermally expands, as the difference of coefficients of thermal expansion between the heater 116 and the rupturable membrane 120 may induce a stress on the rupturable membrane 120. Once rupturable membrane 120 is ruptured, fluid communication between the reservoir 114 and at least one of the plurality of outlets 102 may be opened, as described above. Of course, while a particular type of valve and heater have been described above, it should be understood that any appropriate valve and/or heater may be used as the disclosure is not so limited.

Either prior to, or during the opening of one or more valves of a drug delivery device 100, it may be desirable to pressurize a reservoir 114 of a device including an API disposed therein. For example, a potential energy source 112 may be configured to apply a driving force to a piston 113 either prior to, during, and/or after opening of the one or more valves 110 to drive the piston into the reservoir volume to pressurize the API contained therein. As noted above, in some embodiments, this pressurized API may rupture a softened heater membrane of a valve 110 as part of the opening process of the one or more valves. In either case, once the valves are open and the API reservoir is pressurized, the API may be expelled from reservoir 114 out of the one or more open outlets 102 in the form of one or more jets with a velocity sufficient to penetrate tissue disposed proximate to the associated one or more outlets. As noted previously, the potential energy source 112 may drive the piston through the use of a compressed gas, a pre-loaded spring, a chemical reaction, the sublimation of dry ice, or any other suitable method. Of course, while the use of a piston driven system is illustrated in the figures, it should be understood that any appropriate method and/or system capable of applying a driving force to an API contained in a reservoir may be used as the disclosure is not so limited.

Figure 3:
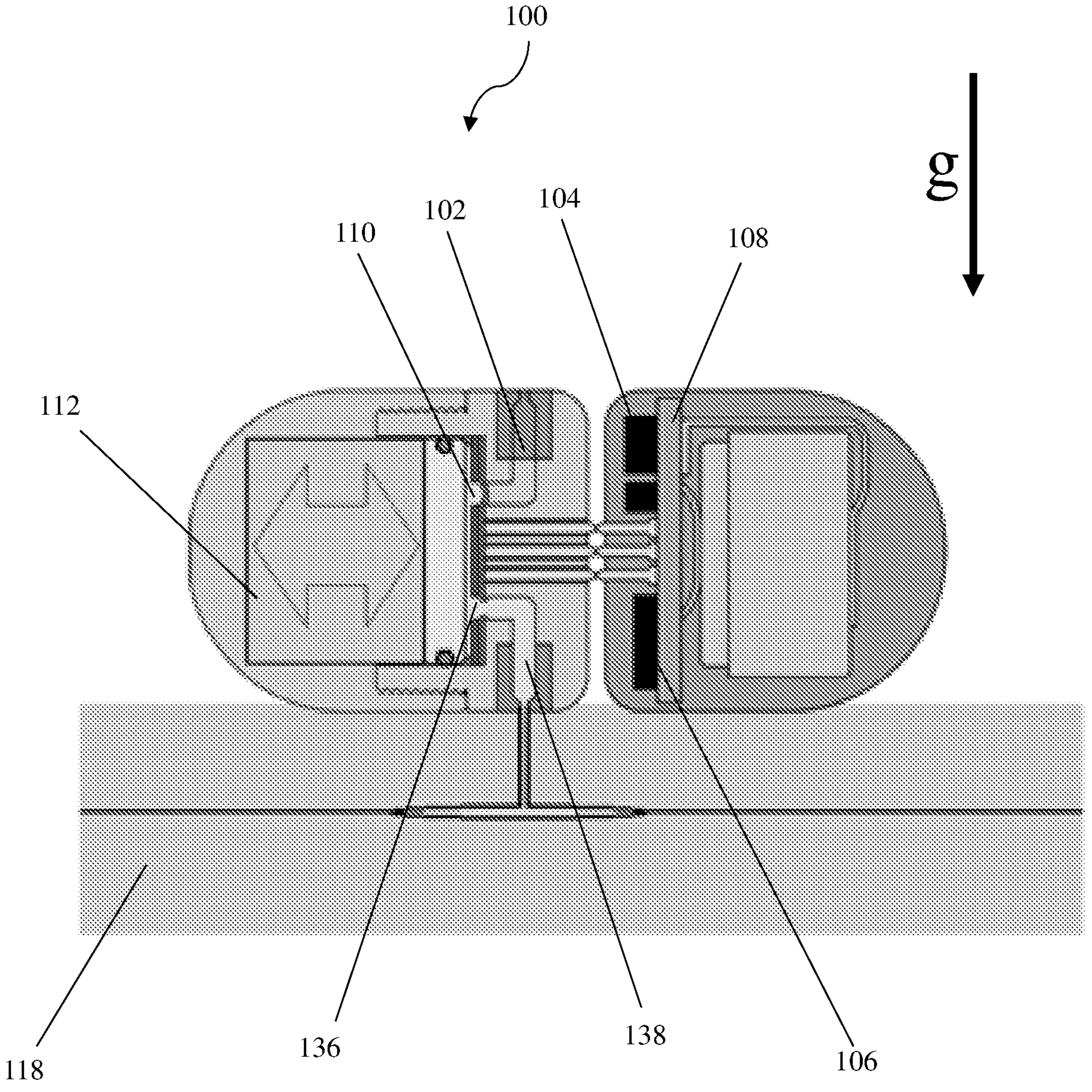
FIG. 3 is a cross sectional view of a drug delivery device according to one illustrative embodiment.

As previously noted, in some embodiments, a drug delivery device 100 may be configured such that the one or more outlets 102 of a device that are opened using the above described valves 110 may be oriented in a desired direction based on the sensed direction of gravity g. FIG. 3 shows one such embodiment of a drug delivery device 100 dispensing an API. Specifically, the API is being jetted into the underlying tissue 118 of an anatomical structure of the subject, such as the submucosal tissue or other tissue of a portion of the gastrointestinal tract of a subject. In this embodiment, the processor 106 has received a signal from the associated sensor 104 regarding the sensed direction of gravity. The processor then opened a particular outlet 138 of the plurality of outlets 102 using any of the above noted methods. Specifically, processor 106 opened a selected valve 136 corresponding to the outlet 138, while keeping the remaining valves of the plurality of valves 110 closed, allowing the API from reservoir 114 to jet out of outlet 138 due to the force applied by potential energy source 112. In this embodiment, the selected one or more outlets are oriented in a direction that includes a component that is parallel, and preferably within a predetermined angle, of the sensed direction of gravity. Again, such an arrangement may be desirable due to it being more likely that tissue is underlying the device in a direction parallel to gravity which may help avoid jetting the API into the intraluminal space within the GI tract away from the mucosa.

Figure 4:
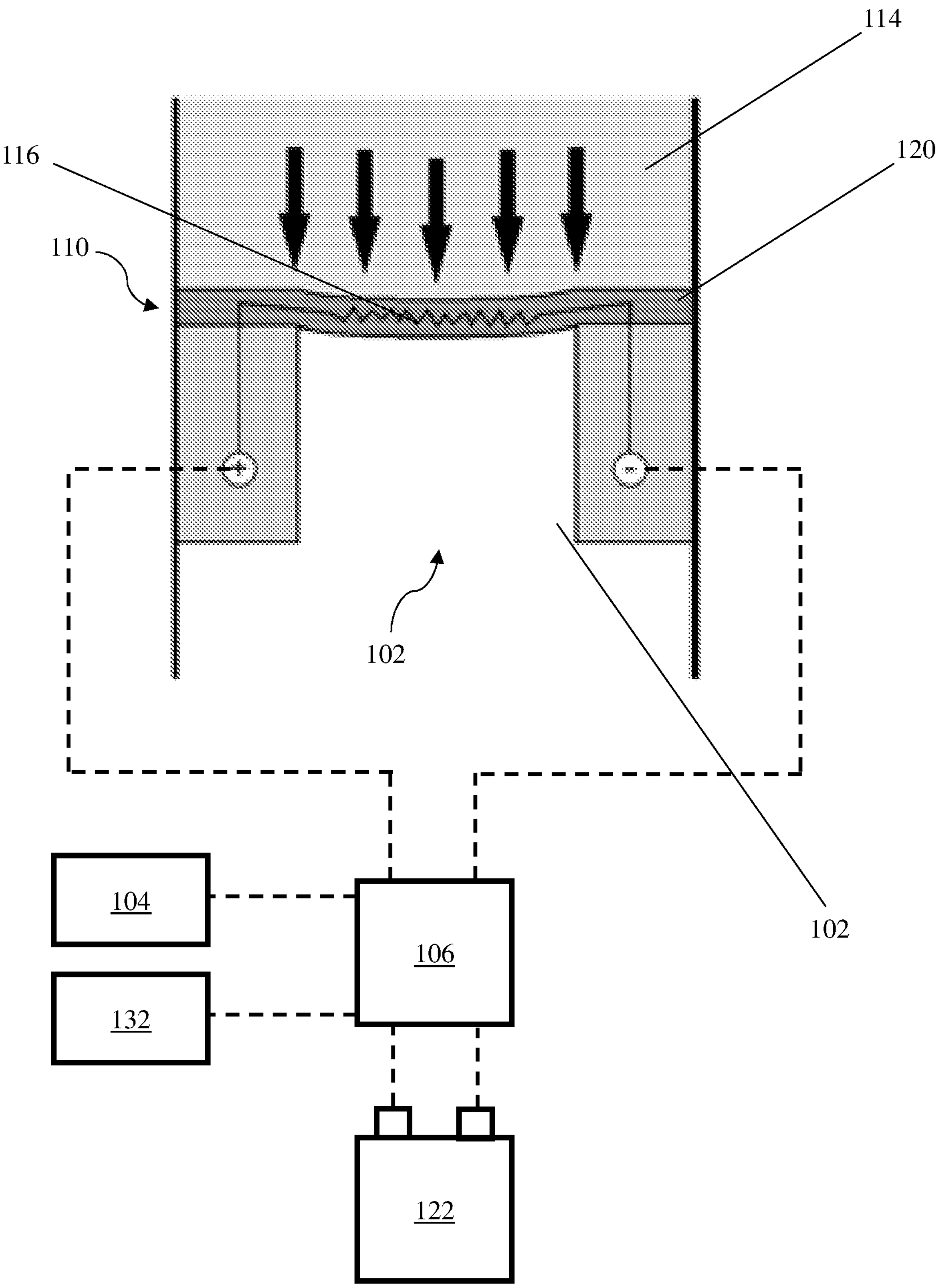
FIG. 4 is a cross sectional view of a rupturable membrane of a drug delivery device according to one illustrative embodiment.

FIG. 4 depicts a schematic embodiment of an outlet 102 associated with a selectively openable valve 110. In the depicted embodiment, a processor 106 may be electrically connected to a sensor 104, a power source 122, and a trigger 132. The processor, or other associated component, may in turn be electronically connected to a heater 116 corresponding to a conductive material embedded in, or disposed on a rupturable membrane 120 as previously described above. Accordingly, the processor 106 may be capable of selectively connecting the power source 122 to the heater 116 to pass a current through the conductive material of the heater to generate heat therein to resistively heat the rupturable membrane 120. Though it should be noted that other types of heaters may be used to heat the membrane.

Figure 5:
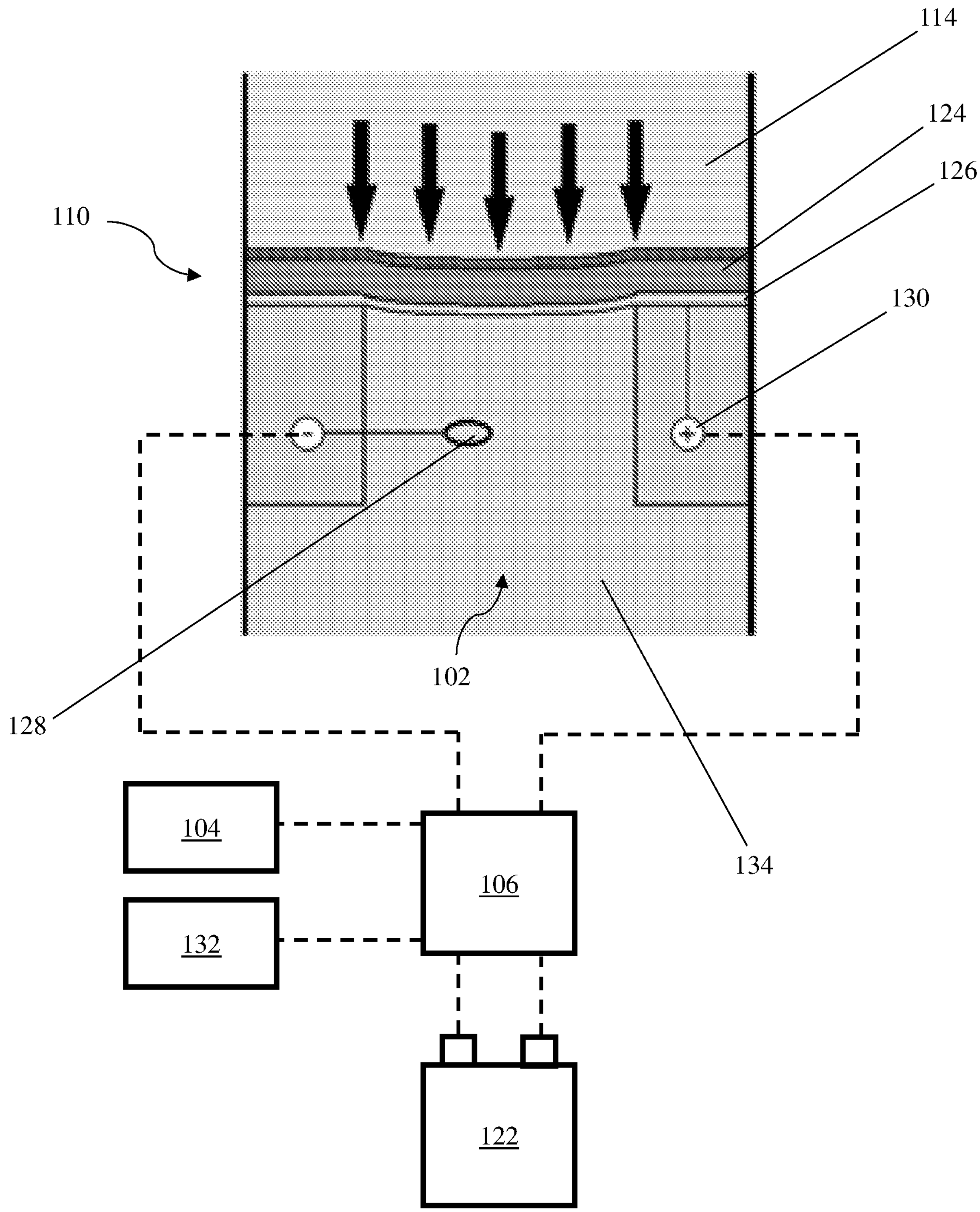
FIG. 5 is a cross sectional view of a rupturable membrane of a drug delivery device according to one illustrative embodiment.

While a heater based valve is described above, valves not including heat rupturable membranes may also be used. For example, as shown in FIG. 5, a valve 110 associated with an outlet 102 may be controlled using electrolytic dissolution of a component disposed along a flow path between an API reservoir and an outlet of the device. In the depicted embodiment, a valve may consist of two layers: a dissolvable membrane 124 that is configured to dissolve upon exposure to one or more predetermined conditions, such as the conditions present in a predetermined portion of the GI tract of a subject (e.g. pH, liquid, etc.); and a conductive support layer 126 disposed beneath and supporting the rupturable membrane. An exterior surface of the support layer disposed opposite from the rupturable membrane may be exposed to an exterior environment including an aqueous medium 134 surrounding the device prior to actuation of the device. The support layer may be substantially stable within the environment of the GI tract such that the support layer does not dissolve while located in a target location of a subject's body. Appropriate materials for the conductive support layer may include, but are not limited to, titanium, gold, and/or any other appropriate conductive material capable of shielding the dissolvable membrane for desired period of time within the gastrointestinal tract of a subject. However, embodiments in which the support layer is initially shielded from the exterior environment, e.g. by a dissolvable coating or plug, are also envisioned. In either case, the dissolvable membrane may be dissolvable by the aqueous medium surrounding the device within a portion of the body, and the support layer may act as a barrier to protect the dissolvable membrane from the aqueous medium.

In the depicted embodiment, a first electrode 126 with a negative polarity that is electrically connected to the processor 106 and/or the power source 122 is exposed to the external environment and the conductive support layer 124 is connected to a second electrode 130 with a positive polarity that is also electrically connected with the processor and/or power source. The processor may control a relative voltage potential applied between the first negative electrode and the conductive support layer and associated second positive electrode during operation such that when the first electrode and the conductive support layer are exposed to a conductive fluid the conductive support layer may be electrolytically dissolved. The electrolytic process may be powered using a constant current, pulsed current, combinations of the foregoing, and/or any other appropriate voltage, power, or current profile. Accordingly, during operation, to open a valve 110 including the above described structure, the processor 106 may apply power from the power source 122 to the first and second electrodes to dissolve the support layer which exposes the dissolvable membrane 124 to the exterior environment. The dissolvable membrane may then come into contact with the aqueous medium 134 and dissolve, thus opening fluid communication between reservoir 114 and the corresponding outlet 102 associated with the depicted valve.

While two specific valve constructions are described above, it should be appreciated that regardless of the particular type of valve used, a drug delivery device may selectively open one or more valves of the device while the remaining valves remain closed to prevent fluid communication between the corresponding outlets and a reservoir of the device. Particularly, the plurality of valves may be configured to withstand a load applied by a medium located within the reservoir when the medium is pressurized by a potential energy source as previously discussed. Thus, when the one or more valves of a device or opened, and API within the reservoir may flow out through the one or more open valves and the corresponding one or more outlets, while the remaining valves and associated outlets of the device remain closed such that the API does not flow through the closed valves and associated outlets.

Regardless of the specific type of valve used to operate a device, a drug delivery device may also include a trigger 132 that is configured to control actuation of the device, see FIGS. 4 and 5. In the depicted embodiment, the trigger is electrically connected with the processor 106 and may be configured in any suitable manner to provide a triggering signal to the processor to operate one or more valves of the device to jet an API into a desired location of a GI tract of a subject. For example, in some embodiments, the trigger 132 may be an electrical timer, a light sensor, an enzymatic sensor, a conductivity sensor, a pH sensor, a pressure sensor, a temperature sensor, a contact sensor, and/or any other appropriate sensor or construction capable of providing a signal to the processor that the device is exposed to one or more predetermined conditions corresponding to a desired target location within the GI tract or other anatomical structure of a subject. Additionally, instances in which dissolvable coatings, plugs, enteric coatings, and/or other components that shields the sensor or other component used to provide a signal to the processor or otherwise actuate operation of the device at the predetermined location may also be used in some embodiments as the disclosure is not limited in this fashion. In either case, in the depicted embodiments, the trigger may provide a signal to the processor to actuate the device once it is located in a desired location.

The drug delivery device may also include features that allow the drug delivery device to select and operate one or more valves 110 of the device based on a sensed direction of gravity. For example, in some embodiments, the drug delivery device 100 may include a sensor 104 configured to sense the direction of gravity. The sensor 104 may send a signal to the processor 106 indicating the sensed direction of gravity. The processor 106 may then select one or more outlets among the plurality of outlets 102 based on the direction of gravity sensed by sensor 104. For example, the processor 106 may select an outlet oriented closest to the direction of gravity sensed by sensor 104, one or more outlets within a predetermined angular threshold of the sensed direction of gravity, or any other appropriate metric. For example, the processor 106 may have a stored set of predetermined parameters (e.g., angular location of each of the plurality of outlets relative to a fixed reference, or any other suitable parameter) related to the position of each outlets of the plurality of outlets 102 stored in a non-transitory processor readable medium connected to the processor. The processor 106 may then compare that stored set of parameters with the sensed direction of gravity to determine which of the one or more outlets has an orientation that is closest to the sensed direction of gravity and/or within a predetermined angular distance of the sensed direction of gravity. For example, without wishing to be bound by theory, the processor 106 may compare the angular orientation of each outlet of the plurality of outlets 102 to the direction of gravity sensed by sensor 104. The processor 106 may then select an outlet with the minimum relative angular displacement between the known position of the outlet and the sensed direction of gravity. The processor 106 may then operate the valve 110 associated with the selected outlet as described above after a triggering signal has been received by an associated trigger 132. Of course, while a particular method of selecting a desired outlet for actuation is described, and a number of different methods for selecting one or more desired outlets for actuation based on a sensed direction of gravity may be used as previously disclosed above.

In the embodiments of FIGS. 4 and 5, the processor 106 and trigger 132 are not shown as being connected with a potential energy source (not depicted) used to pressurize the reservoir 114. In such an embodiment, the reservoir may be pre-pressurized by a preloaded spring, compressed gas, or other structure such that once the associated valve 110 is open, the API may flow out of the reservoir through the open outlet 102. However, embodiments in which the processor is also operatively connected to an actuated potential energy source such that the processor also actuates operation of the potential energy source to pressurize the reservoir are also contemplated. For example, the processor may electrically trigger a reaction, actuate a lock to release a spring or associated piston, or any other appropriate configuration capable of actuating the potential energy source either prior to, simultaneously with, or after opening one or more desired valves of the device. Alternatively, a separate trigger, such as a dissolvable plug or coating, may be separately associated with the potential energy source as the disclosure is not limited to specifically how the timing of the actuation of the potential energy source and valves of the device are coordinated.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided as a single processor or multiple processors. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the embodiments described herein may be embodied as a processor readable storage medium (or multiple computer readable media) (e.g., a computer memory, one or more floppy discs, compact discs (CD), optical discs, digital video disks (DVD), magnetic tapes, flash memories, RAM, ROM, EEPROM, circuit configurations in Field Programmable Gate Arrays or other semiconductor devices, or other tangible computer storage medium) encoded with one or more programs that, when executed on one or more computers or other processors, perform methods that implement the various embodiments discussed above. As is apparent from the foregoing examples, a processor readable storage medium may retain information for a sufficient time to provide processor-executable instructions in a non-transitory form. Such a processor readable storage medium or media can be transportable, such that the program or programs stored thereon can be loaded onto one or more different computing devices or other processors to implement various aspects of the present disclosure as discussed above. As used herein, the term "processor-readable storage medium" encompasses only a non-transitory processor-readable medium that can be considered to be a manufacture (i.e., article of manufacture) or a machine. Alternatively or additionally, the disclosure may be embodied as a processor readable medium other than a computer-readable storage medium, such as a propagating signal.

The terms "program" or "software" are used herein in a generic sense to refer to any type of computer code or set of computer-executable instructions that can be employed to program a computing device or other processor to implement various aspects of the present disclosure as discussed above. Additionally, it should be appreciated that according to one aspect of this embodiment, one or more computer programs that when executed perform methods of the present disclosure need not reside on a single computing device or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. An article configured for administration to a subject, the article comprising:

- a reservoir configured to contain an active pharmaceutical ingredient;
- a plurality of outlets;
- a plurality of valves, wherein each outlet of the plurality of outlets is in selective fluid communication with the reservoir through an associated valve of the plurality of valves;
- a sensor configured to sense a direction of gravity; and
- a processor configured to receive a signal from the sensor, wherein the processor is configured to selectively operate one or more of the plurality of valves to dispense the active pharmaceutical ingredient through one or more of the plurality of outlets based at least in part on the sensed direction of gravity.

2. The article of claim 1, wherein the one or more of the plurality of valves is oriented at least partially vertically downwards relative to the sensed direction of gravity.

3. The article of claim 1, wherein the one or more of the plurality of valves is oriented in a direction that is within 45° or less of the sensed direction of gravity.

4. The article of claim 1, further comprising a potential energy source configured to apply a pressure to the reservoir to dispense the active pharmaceutical ingredient through the one or more of the plurality of outlets.

5. The article of claim 4, wherein the potential energy source is compressed gas.

6. The article of claim 4, wherein the potential energy source is a spring.

7. The article of claim 4, wherein the potential energy source includes a reaction chamber.

8. The article of claim 4, wherein the potential energy source is an explosive material.

9. The article of claim 1, wherein each one of the plurality of valves includes a heat rupturable membrane and a heater configured to heat the heat rupturable membrane.

10. The article of claim 9, wherein the heater is a resistive heater disposed in and/or on the heat rupturable membrane, and wherein the processor is further configured to selectively apply a current to resistive heaters of individual valves of the plurality of valves to selectively operate the one or more of the plurality of valves.

11. The article of claim 1, wherein each one of the plurality of valves includes a dissolvable membrane disposed on a conductive support layer, and wherein the conductive support layer is configured to be electrolytically dissolved.

12. The article of claim 11, further comprising a first negative electrode configured to be exposed to an exterior of the article, and a second positive electrode electrically connected to the conductive support layer.

13. The article of claim 12, wherein the processor is further configured to selectively apply a voltage potential between the first negative electrode and the conductive support layer to electrolytically dissolve the conductive support layer.

* * * * *